(12) United States Patent
Turicchia et al.

(10) Patent No.: US 8,708,923 B2
(45) Date of Patent: Apr. 29, 2014

(54) WEARABLE SYSTEM FOR MONITORING PHYSIOLOGICAL SIGNALS

(75) Inventors: Lorenzo Turicchia, Cambridge, MA (US); Soumyajit Mandal, Cambridge, MA (US); Rahul Sarpeshkar, Arlington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 503 days.

(21) Appl. No.: 12/700,214

(22) Filed: Feb. 4, 2010

(65) Prior Publication Data
US 2010/0198094 A1 Aug. 5, 2010

Related U.S. Application Data

(60) Provisional application No. 61/149,801, filed on Feb. 4, 2009.

(51) Int. Cl.
*A61B 5/04* (2006.01)

(52) U.S. Cl.
USPC .......................................... 600/508

(58) Field of Classification Search
USPC .................................... 600/509, 508
See application file for complete search history.

(56) References Cited

U.S. PATENT DOCUMENTS 7,558,622 B2 * 7/2009 Tran .............................. 600/509

OTHER PUBLICATIONS

Tavakoli et al., "An Ultra-Low-Power Pulse Oximeter Implemented With an Energy-Efficient Transimpedance Amplifier " IEEE Transactions on Biomedical Circuits and Systems, 2009, pp. 1-13.

* cited by examiner

*Primary Examiner* — Eric D. Bertram
(74) *Attorney, Agent, or Firm* — Gesmer Updegrove LLP

(57) ABSTRACT

A wearable system for monitoring a plurality of physiological signals is provided. The wearable system includes at least one sensor producing the physiological signals associated with a patient. A processor unit receives the physiological signals from the at least one sensor. The processor unit analyzes the physiological signals to determine the occurrence of a triggered event and produces at least one output signal identifying the triggered event. A transmission unit receives the at least one output signal and prepares for transmission of the at least one output signal.

14 Claims, 9 Drawing Sheets

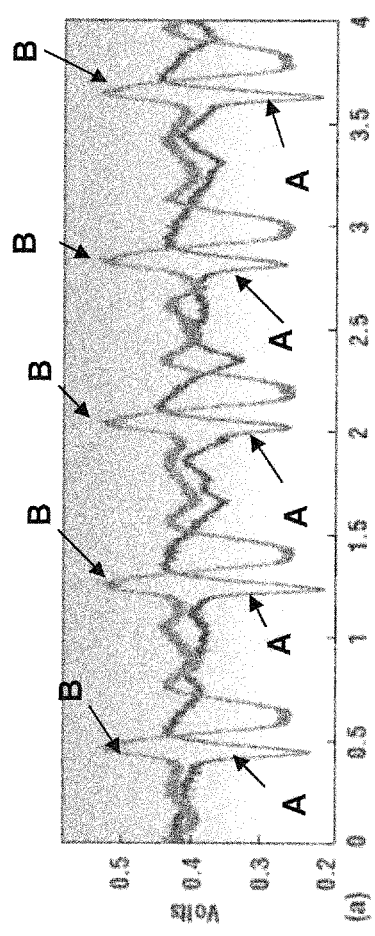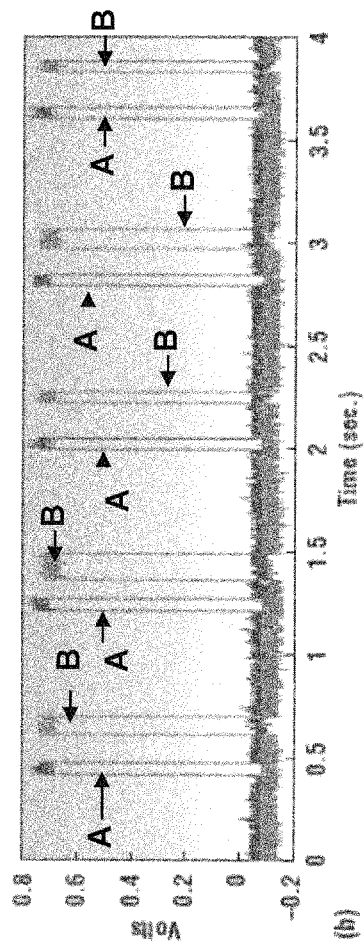
FIG. 6A
FIG. 6B

WEARABLE SYSTEM FOR MONITORING PHYSIOLOGICAL SIGNALS

PRIORITY INFORMATION

This application claims priority from provisional application Ser. No. 61/149,801 filed Feb. 4, 2009, which is incorporated herein by reference in its entirety.

BACKGROUND OF THE INVENTION

The invention is related to the field of sensors, and in particular to a wearable system for monitoring physiological signals.

With the world population aging rapidly, providing care for the elderly is becoming an increasingly important problem. For instance, more than 5,000 people experience Sudden Cardiac Arrest (SCA) every week in the United States alone. The only definitive treatment for SCA is early defibrillation: no more than 6 minutes from arrest to first shock. The chance for survival drops 10% per minute without defibrillation, and today, over 95% of SCA victims die. Since automatic defibrillators are increasingly available, pervasive monitoring of those at risk can save many lives. Infants constitute another segment of the population where pervasive monitoring could enable rapid responses to life-threatening situations. In the United States alone, approximately 2,000 infants die each year from Sudden Infant Death Syndrome (SIDS). Since slow heart-rate (bradycardia) is an important indicator of SIDS, early detection of bradycardia in infants can save many lives each year.

Wireless networks of context-aware body-mounted sensors have come into prominence recently for pervasive patient monitoring. However, to be effective, monitoring systems should be unobtrusive, robust, and low-cost.

SUMMARY OF THE INVENTION

According to one aspect of the invention, there is provided a wearable system for monitoring a plurality of physiological signals associated with a patient. The wearable system includes at least one sensor producing the physiological signals. A processor unit receives the physiological signals from the at least one sensor. The processor unit analyzes the physiological signals to determine the occurrence of a triggered event and produces at least one output signal identifying the triggered event. The processor unit is operable for harvesting RF energy to power the wearable system or only said at least one sensor. A transmission unit receives the at least one output signal and prepares for transmission of the at least one output signal.

According to one aspect of the invention, there is provided a wearable system for monitoring a patient. The wearable system includes a first microphone for detecting environmental sounds and outputting a first signal. A second microphone detects the patient's physiological status or environmental sounds and produces a second signal. A processor unit receives the first signal and second signal. The processor unit analyzes the first signal and the second signal to determine the occurrence of a triggered event and produces at least one output signal identifying the triggered event. A transmission unit receives the at least one output signal and prepares for transmission of the at least one output signal.

According to another aspect of the invention, there is provided a method for remotely monitoring a plurality of physiological signals using a wearable system. The method includes providing at least one sensor producing the physiological signals associated with a patient. Also, the method includes receiving the physiological signals from the at least one sensor using a processor unit. The processor unit analyzes the physiological signals to determine the occurrence of a triggered event and produces at least one output signal identifying the triggered event. Also, the processor unit harvests RF energy for powering the wearable system or only said at least one sensor. Moreover, the method includes sending the at least one output signal to a transmission unit for transmission.

BRIEF DESCRIPTION OF THE DRAWINGS

FIGS. 6A-6B are PCG and PPG waveforms measured at the wrist and fingertip using an oximeter;

DETAILED DESCRIPTION OF THE INVENTION

The invention provides a low-power, battery-free tag for use in pervasive sensing applications such as wearable patient-monitoring systems or body sensor networks. The tag includes of a custom integrated circuit, an antenna for RF energy harvesting, and several sensors for monitoring important physiological parameters and generating alarms when necessary. By using several physiological signals and/or multiple sensors, one can reduce the risk of false alarms being generated. The chip can include four independently-programmable channels that generate asynchronous spikes when biomedical signals cross a programmable threshold voltage. Spike duration and maximum spiking rate are also programmable. Spikes on different channels can be combined using a programmable logic array (PLA). Each channel can also actuate an external sensor by supplying DC current. When not powering external sensors, the chip consumes only 1.0 µW of power. Experimental results with phono-cardiogram (PCG) and photo-plethysmogram (PPG) signals show the effectiveness of the invention. It has been also demonstrated that one can localize the tag to within 0.6 m by using an audio localization scheme.

Figure 1:
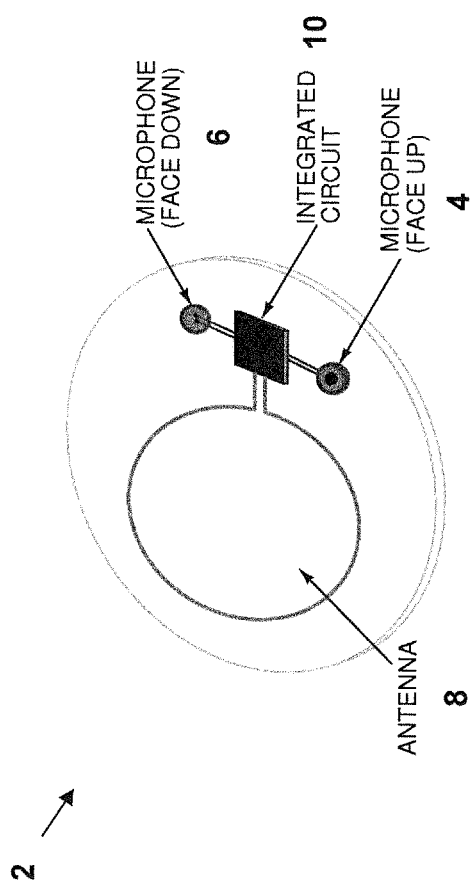
FIG. 1 is a schematic diagram illustrating an embodiment of the invention having two microphones and an antenna attached to a flexible, adhesive surface.

The invention uses multiple sensors to generate three types of alarm: disconnection from the body, device malfunction, and patient emergency. For example, FIG. 1 shows an example of a patient-monitoring tag system 2 having two microphones 4, 6, one facing up 4 (away from the body) and the other facing down 6. The downward-facing microphone 6 monitors heart sounds, while the upward-facing microphone 4 is usually switched off to save power. It is turned on only when the downward-facing microphone 6 does not detect any heart sounds and a disconnection or patient emergency is suspected. If both microphones 4, 6 now pick up similar environmental sounds, a 'disconnection alarm' is generated since it is probable that the tag is no longer in proximity to the skin. A 'patient emergency alarm' is generated if the downward-facing microphone 6 does not pick up environmental sounds, but the upward-facing microphone 4 does, since in this case it is likely that the tag 2 is still attached and the heart has stopped. If neither microphone 4, 6 picks up any sounds, the tag is probably malfunctioning; therefore a 'device malfunction alarm' is generated.

Each tag contains a unique identification code and powers up using harvested RF power. A fixed base station communicates with multiple tags and decides, based on transmitted patient data, if an alarm should be triggered. Such a system will be useful for hospitals, facilities that care for infants and the elderly, and also ordinary homes. In order to quickly cover a large fraction of the population at risk one needs to keep the tag low-cost (ideally, less than $2 each when manufactured in volume), disposable, small and easy to use. A low-power custom integrated circuit or chip 10 is used that forms the central component of the patient-monitoring tag 2 and demonstrate its power harvesting, sensing and actuation capabilities.

Figure 2:
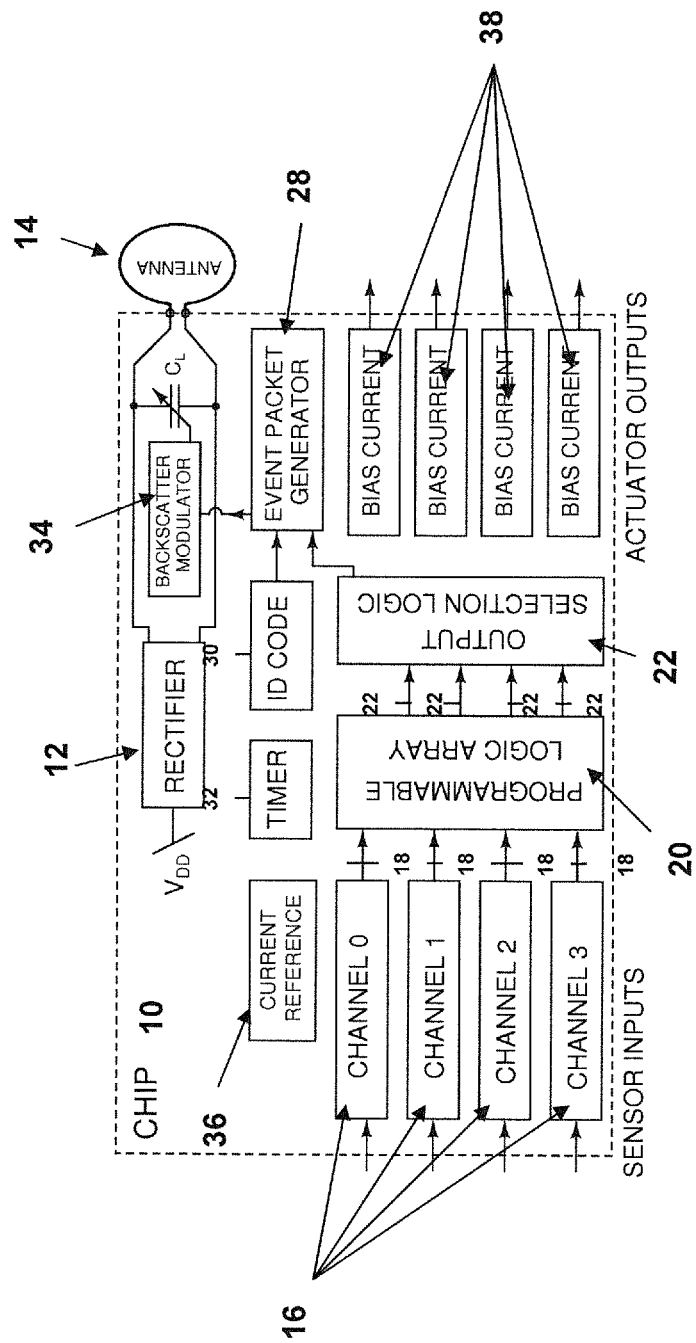
FIG. 2 is a schematic block diagram illustrating a low-power patient-monitoring integrated circuit or chip.

A block diagram of the integrated circuit or chip 10 is shown in FIG. 2. It was designed to be extremely low power by incorporating only minimally acceptable amounts of computation and signal processing, most complexity is transferred to the fixed base station. The chip 10 can harvest radiated RF power, making a low-cost battery-free tag possible. An efficient two-stage CMOS rectifier 12 is connected to an external loop antenna 14. The input capacitance of the chip 10, $C_L$ resonates with the inductive input reactance of the antenna at the operating frequency. The resultant L-type impedance match provides passive voltage gain that reduces the amount of RF power needed to overcome the dead-zone of the rectifier 12, thereby increasing operating range. The first rectifier stage is designed to have low output impedance since it powers up external sensors, which typically consume much more power than the chip itself. The second stage, which provides a higher-impedance output, is used to power up ($V_{DD}$) the chip 10. Over-voltage protection circuits at the power supply and RF input nodes prevent damage due to large RF amplitudes.

One can now calculate $P_A$, the RF power that can be harvested at different distances D from the transmitter. Path loss models predict the fall-off of radiated power density Pr (in W/m2) with D. A simple version commonly used for modeling indoor environments recognizes two zones: Pr proportional to $D^{-n1}$ for D<D0, and Pr proportional to $D^{-n2}$ for D>D0, where D0, n1 and n2 are constants. Typically n1 is approximately equal to 2, the free-space value, and n2 varies between 2.5 and 4. The value of n2 exceeds 2 because of absorption and reflection of the RF by environmental obstacles, such as furniture and people. The following conservative values: D0=5 m, n1=2, n2=3.5 are used.

Figure 3:
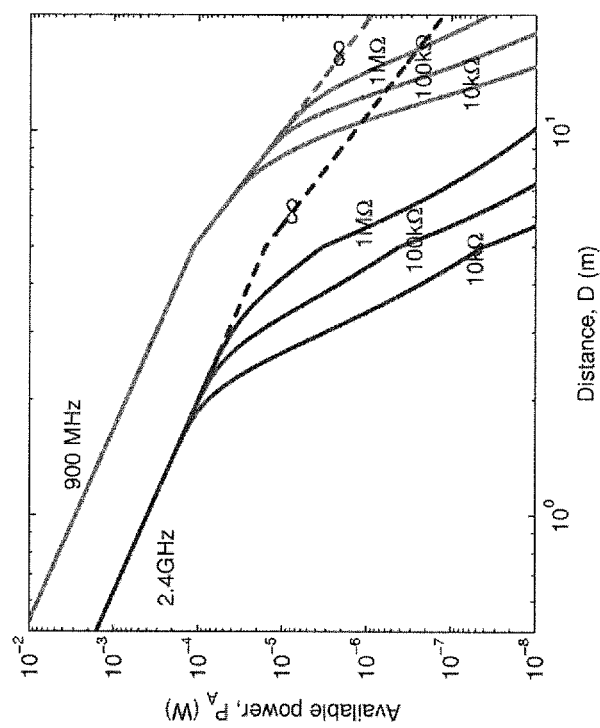
FIG. 3 is a graph illustrating harvested RF power available as a function of distance from the transmitter for different load resistances at 900 MHz and 2.4 GHz.

Combining the predicted path loss with the rectifier model gives us FIG. 3. FIG. 3 assumes that the equivalent isotropic radiated power (EIRP) is 4 W, which is the maximum allowed in the United States for radio-frequency identification (RFID) applications. It shows $P_A$ as a function of D at two popular RFID frequencies: 900 MHz and 2.4 GHz. The main reason for going to higher operating frequencies is to reduce the physical size of the antenna. Loop antennas are normally operated at their first resonant frequency. At this frequency the circumference of the loop is half the wavelength. Therefore a single-turn circular loop has a diameter of 5.3 cm at 900 MHz and 2.0 cm at 2.4 GHz. Multiple-turn loops can be used to reduce antenna size at the cost of increased fabrication complexity.

The various curves in FIG. 3 correspond to different load resistances $R_L$ driven by the rectifier. They decrease rapidly at large distances because the received RF amplitude becomes smaller than the rectifier's dead zone. The load resistance is usually dominated by the power consumed by off-chip sensors and not the chip itself. For example, a microphone biased at 30 μA and 0.5V (typical values used in our experiments) dissipates 15 μW, corresponding to an effective load driven by the rectifier of $R_L$=16.7 kOhm.

FIG. 3 then predicts an operating range of approximately 12 m at 900 MHz and 3 m at 2.4 GHz. In practice the reliable operating range will be somewhat smaller because some tags will be mistuned by their proximity to conductive and dielectric surfaces. In addition, one has to allow for transient drops in received RF power level (fades), which are ubiquitous in indoor environments because the received signal is the superposition of multiple waves with time-varying amplitude and phase. Nevertheless, a single base-station operating at 900 MHz is sufficient for a moderately-sized room.

The chip 10 includes four independent channels 16 that can be used to interface with various types of sensors. The outputs 18 of these channels 16 are digital spikes, i.e., 'event' signals. These signals can be combined in a flexible way using a programmable logic array (PLA) 20 that can implement a variety of Boolean logic functions. In this case, the PLA 20 is a four-input four-output design with an 8×8 AND plane and a 4×8 OR plane. The PLA 20 allows implementing any of the 216 possible logic functions of four inputs 18 for any of its four outputs 22 in a programmable fashion. These outputs 22 can be monitored individually, allowing us to implement rudimentary sensor-fusion algorithms that combine the outputs of multiple channels. Programmable output selection logic 24 multiplexes the four PLA outputs 22 into a single signal that is transmitted to the base station as "event packets" using the event packet generator 28 that includes a chip identification code 30 and time stamps provided by a timer 32. Data is transmitted using a backscatter modulator 34 that includes a 100 fF capacitor being added and subtracted from $C_L$ to change the amount of RF power scattered by the tag. Backscatter modulation is popular in passive RFID systems because all the complexity and power consumption is pushed to the base station, the tag remains simple and low-power. A current reference source 36 provides current to one or more bias current circuits 38 producing bias current to power up other sensors.

Figure 4:
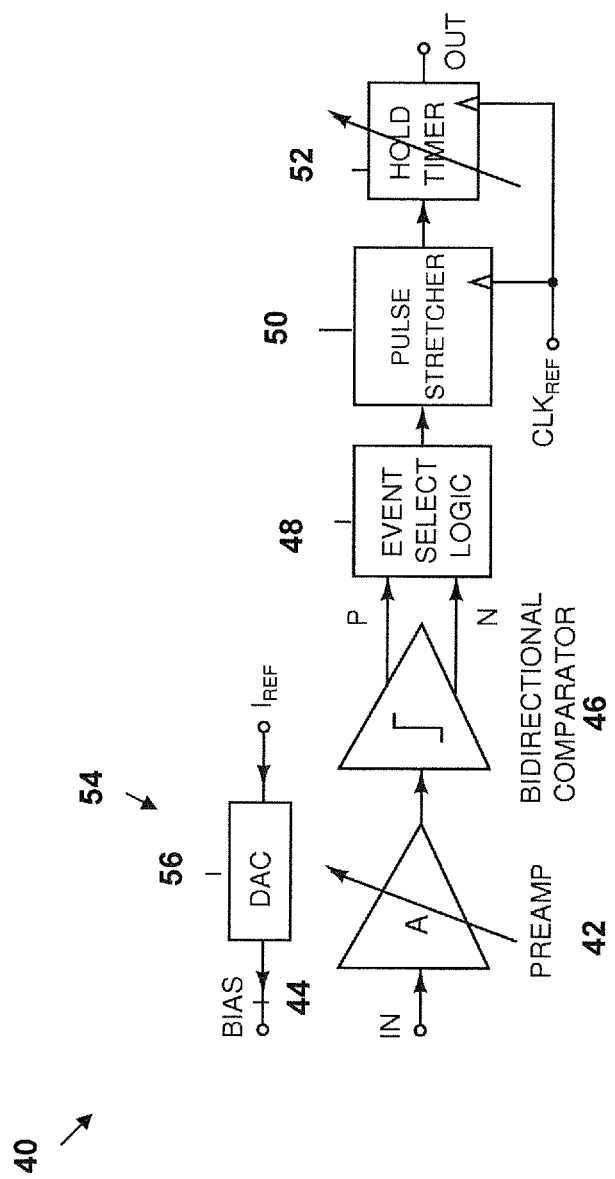
FIG. 4 is a schematic block diagram illustrating a single signal-processing channel used in accordance.

A block diagram of a single channel 40 is shown in FIG. 4. The preamplifier 42 includes a common source stage with capacitive feedback. The size of the feedback capacitor can be varied between C0 and 16C0 to set the gain. The amplifier 42 incorporates DC rejection, i.e., the transfer function is bandpass with a very low cut-in frequency (typically <1 Hz). It uses a nominal bias current 44 of 10 nA and C0=0.5 pF resulting in a bandwidth that decreases from 12 KHz to 6 KHz as the gain increases from 1 to 16. A matched copy of the amplifier (minus the capacitors) is used to determine the quiescent operating point.

The comparator 46 generates events whenever the output voltage of the amplifier 42 differs from its quiescent value by more than a fixed threshold voltage Vth=80 mV. There are two types of events: positive-going, when the output voltage is larger than its quiescent value by Vth or more, and negative-going, when it is smaller. The smallest input amplitude that triggers a spike decreases from Vth to Vth/16 (80 mV to 5 mV) as the preamplifier 42 gain increases from 1 to 16.

Event selection logic 48 is connected to the comparator output in each channel P,N and allows only positive or negative-going spikes, both, or neither to be detected. This combinational block 48 is followed by a pulse-stretcher circuit 50 that adds hysteresis in the time domain to prevent multiple comparator transitions due to noise when an event is detected. It also ensures that output spikes always last long enough for at least one complete data packet to be broadcasted during every spike. The pulse-stretcher circuit 50 is a digitally-timed one-shot. It allows an incoming event edge to set its output high, and a delayed version of this edge to reset it low.

The pulse-stretcher circuit 50 is followed by a programmable hold timer circuit 52. This circuit 52 imposes a hold time Thold after each spike, during which no new spikes can be generated. By placing an upper bound of 1/Thold on the spiking rate, the hold timer circuit 52 greatly reduces the probability of timing collisions between different tags. The average value of Thold can be varied between 94 ms and 1.4 s.

A programmable DC current source 54 was designed for every channel. This current source 54 can be used to power up external sensors, such as microphones, and includes a 8-bit binary-weighted current DAC that can supply between 0.5 $\mu$A and 128 $\mu$A of BIAS current 44 depending on the input current Iref. To reduce power consumption, the chip was designed to operate on power supply voltages as low as 0.8V (core) and 0.5V (programmable current sources).

An on-chip serial interface allows the user to program the PLA 20, channel selection logic 12, 16-bit chip identification code 30, and channel parameters such as sensor current, preamplifier gain and hold time. The static power consumption with no external sensors is only 10 $\mu$W. The power consumption with sensors presented depends on their bias currents, which are application-dependent.

The invention can use a microphone to detect heart sounds. Commercial microphones contain built-in JFET preamplifiers. The microphone is biased at much lower currents than recommended by the manufacturer to save power. In this regime the JFET is unsaturated and acts as a voltage-controlled resistor, making signal gain proportional to the bias current. By varying with the on-chip DAC one can trade-off sensitivity with bandwidth and power consumption. In practice one can save considerable amounts of power because heart sounds are relatively loud and low in bandwidth (typically, 20-250 Hz). A Panasonic omnidirectional electret condenser microphone (WM-63PR) in a plastic enclosure is used. The WM-63PR was selected since it is a small, thin device (diameter=6 mm, thickness=1.3 mm) that is also cheap. Similar microphones that are even cheaper can also be used since sound quality is not critically important.

Microphones are normally placed on the chest for monitoring heart activity. However, the microphone membrane cannot vibrate freely if it is directly attached to the skin. Therefore one can add a small air chamber (approximately 1 mm thick) below the sensor. The chamber has no vents, reducing the amount of ambient noise, but its diameter and shape have little effect on sound pickup.

Microphones are biased using on-chip current sources operating on a 0.5V supply. In the first case, two microphones are connected to channels on the chip and attached to the neck and wrist of a subject. These positions were selected since a strong pulse was expected at these locations. Each microphone is biased at 30 $\mu$A and the preamplifier gain was set to 8. In other cases, the sensor was placed at its default position, the chest. In this position heart sounds are louder, enabling the microphone bias current to be further reduced. Note other types of sensors beside microphones can be used, such as piezo-electric transducers.

Figure 5A:
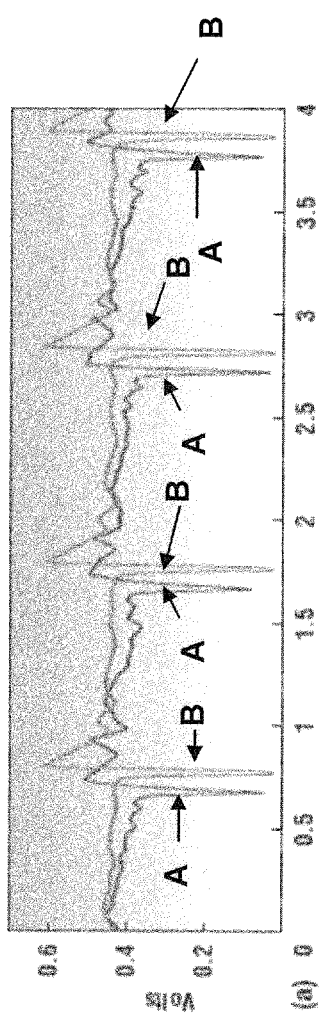
FIGS. 5A-5B are PCG and PPG waveforms measured at the wrist and fingertip.
Figure 5B:
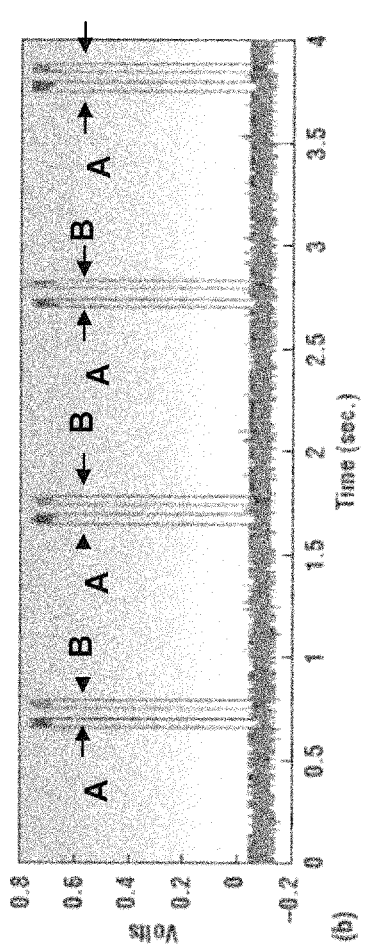

FIGS. 5A-5B are PCG (A) and PPG (B) waveforms measured at the wrist and fingertip, respectively. In particular FIG. 5A shows the preamplifier analog output within each channel and FIG. 5B shows the final digital event, or spike, that each channel generates. The waveform A at the wrist is delayed relative to the waveform B at the neck by about 95 ms because of the time taken by the systolic pulse to propagate down the length of the arm. This delay can be used to provide information about blood pressure. Each large negative spike is caused by the systolic upsurge in blood pressure and consequent dilation of the arteries. There are two reasons why the high-frequency components found in a conventional PCG (A) waveform are almost completely absent in these recordings. Firstly, the coupling between the skin and the microphone is a low-pass filter. Secondly, microphone sensitivities were deliberately kept low by reducing their bias currents. This was because heart rate information was of interest, which resides in the loud, low-frequency components of the PCG (A) (from 10-80 Hz).

Also, one can combine the wrist microphone (still biased at 30 $\mu$A) with an external pulse oximeter connected to another channel. The oximeter, which is used to measure oxygen saturation level in the blood, is attached to the index finger of the subject. Pulse oximeters can also be used to measure variations in the optical density of transmission in the arteries due to their contraction and relaxation as a function of time. Such a recording is known as a photo-plethysmogram, or PPG. For simplicity, one can use an off-the-shelf infra-red LED light source and a Texas Instruments OPT101 photosensor. The OPT101 includes a photodiode and transimpedance amplifier integrated into a single package. Its output is fed into the chip 10. FIGS. 6A-6B are PCG (A) and PPG (B) waveforms measured at the wrist and fingertip, respectively. In particular FIG. 6A shows the preamplifier analog output within each channel and FIG. 6B shows the final digital event, or spike, that each channel generates. The peaks in the PPG (B) waveform line up with the negative spikes in the PCG (A) because it is recorded from adjacent locations, i.e., the pulse propagation delay from the wrist to the finger is small.

As a final example of the chip's capabilities, one can demonstrate that it can be localized within a room using acoustic time-of-flight measurements. Such a system will only be turned on during a suspected patient emergency to aid in localizing the patient and also possibly providing an audio alarm. One can use a single microphone attached to the chip and two speakers (L and R) placed a distance d apart. By measuring the time delays t1 and t2 between when each speaker beeps and the chip starts generating spikes, one can locate the position of the microphone in two dimensions.

The microphone was biased at 128 $\mu$A and preamplifiers from two channels are cascaded to give a total gain of 8×12=96. Small, cheap speakers are placed d=12 ft apart and programmed to transmit 100 ms tone bursts at 230 Hz. The burst frequency was kept as low as possible to minimize audibility and attenuation with distance, but was limited by the poor low-frequency response of the small speakers being used. The bursts were spaced 400 ms apart to ensure that all echoes from the first burst would die down before the second one arrived. The measured sound level at the center of the room with either speaker on was 87 dB SPL, which is loud enough to serve as an alarm signal.

The propagation times t1 and t2 from the speaker to the microphone are estimated by measuring the time between the onset of each burst and the first spike detected by the chip.

These times were estimated using a simple threshold-based algorithm. The distances of the microphone from each speaker are given by d1=ct1 and d2=ct2, where c=1130 ft/s is the speed of sound in air.

Figure 7:
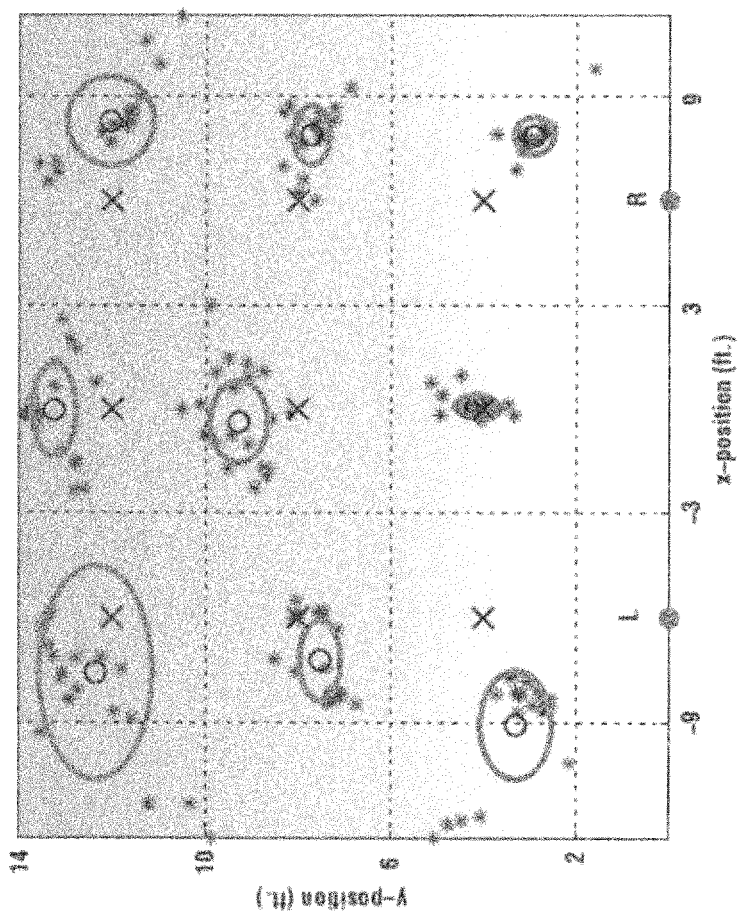
FIG. 7 is a schematic diagram illustrating measured microphone positions produced in accordance with the invention.

The measured microphone positions are shown in FIG. 7 for 9 different positions and 20 trials. The average standard deviation in the measured positions was 1.4 ft (0.43 m), and the average error between the measured and actual positions was 1.97 ft (0.6 m). Positions closer to the speakers were more accurately measured than distant ones because of the realistic indoor environment, which included sound propagation barriers in the shape of furniture and people. The current accuracy of the system already provides important information about the location of the patient. For example, one can distinguish between the bed, a chair and the bathroom. Accuracy can be further increased if necessary by using a higher transmission frequency to improve timing precision. However, since propagation losses increase with frequency, louder sounds are needed. An attractive alternative in this context is to use ultra-sound. Finally, the localization strategy can be easily extended to three dimensions by adding a third speaker.

The audio alarm and localization technique that has been described can be extended to other wireless sensor applications. For example, it can form the basis for sensor-fusion algorithms where sensors such as video cameras that provide high-bandwidth information can be activated by the audio alarm only when abnormal events are detected. The amount of information that needs to be continuously monitored by a human operator is thereby reduced.

Figure 8:
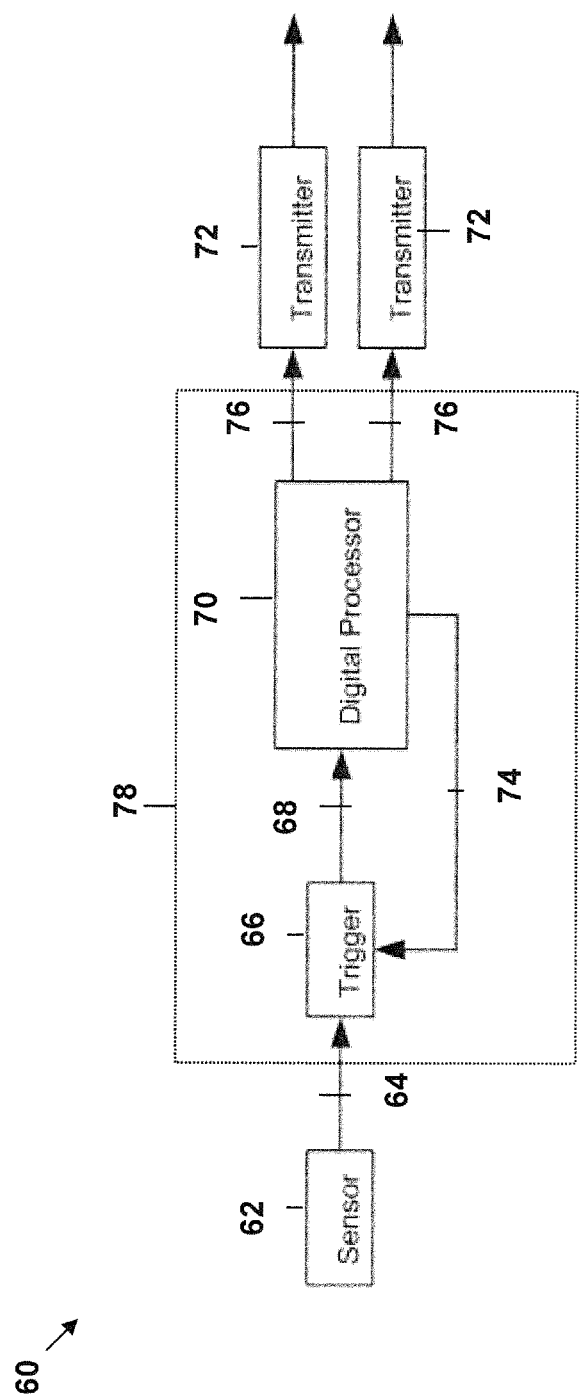
FIG. 8 is a schematic block diagram illustrating another embodiment of the invention.

FIG. 8 is a schematic block diagram illustrating another embodiment of the invention. In particular, FIG. 8 shows a wearable patient-monitoring tag system 60 having a sensor 62 providing a signal 64 to be received by a trigger module 66. The trigger module 66 analyzes the signal 64 to determine if it includes values that can trigger an event to a base station and then outputs a signal 68. A digital processor 70 receives the signal 68 and performs the necessary digital operations to allow the contents of the signal 68 to be transmitted by outputting one or more signals 76 to one or more transmitters 72. Note the digital processor can adjust the properties of the trigger module using a signal 74. Also, the trigger module 66 and digital processor 70 and their respective output signals 68, 76 form a processor structure 78 that can either be an integrated circuit or chip.

Figure 9:
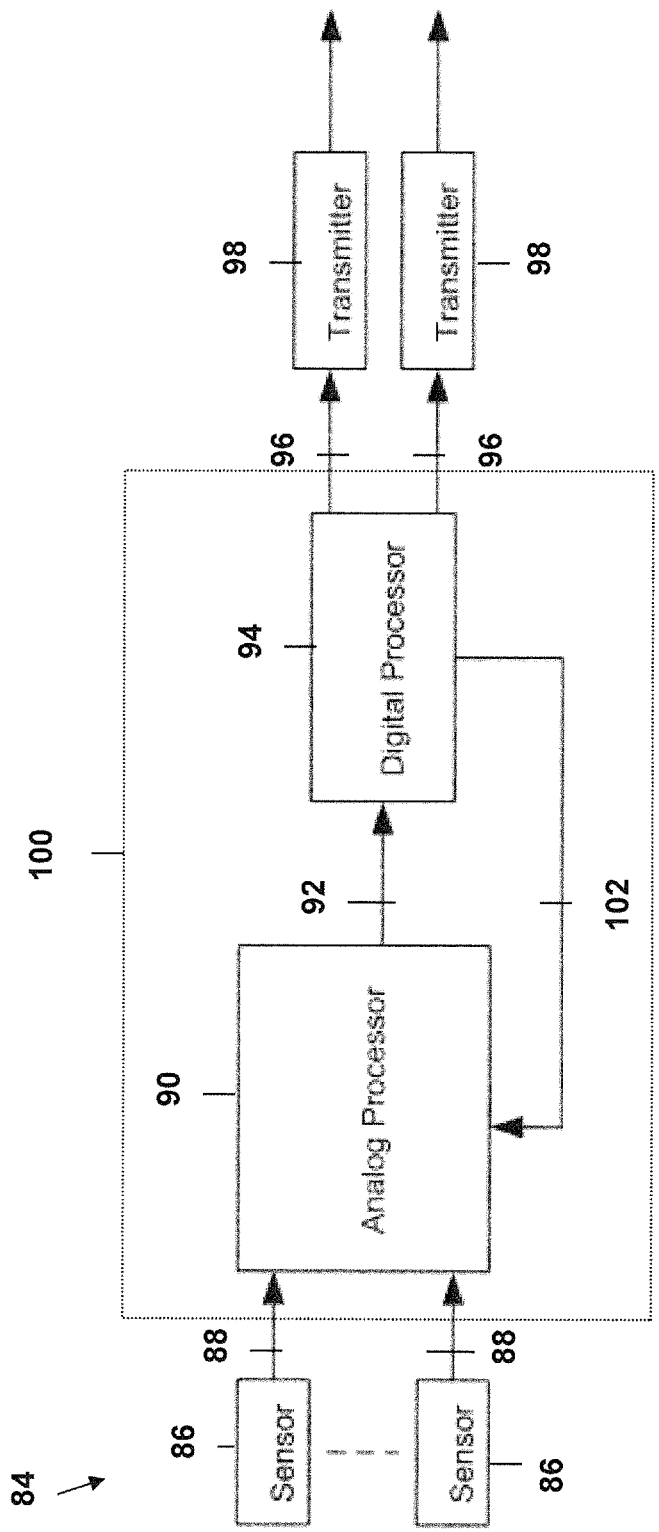
FIG. 9 is a schematic diagram illustrating another embodiment of the invention using one or more sensors and an analog processor.

FIG. 9 is a schematic diagram illustrating another embodiment of the invention using one or more sensors and an analog processor. In particular, FIG. 8 shows a wearable patient-monitoring tag system 84 having one or more sensors 86 providing one or more signals 64 to be received by an analog processor 90. The analog processor 90 analyzes the signal 88 to determine if it includes values that can trigger an event to a base station and then outputs a signal 92. A digital processor 94 receives the signal 92 and performs the necessary digital operations to allow the contents of the signal 92 to be transmitted by outputting one or more signals 96 to one or more transmitters 98. The digital processor 94 can adjust the properties of the analog processor 90 using a signal 102. Note that the trigger module is not shown explicitly but it can to be included within either the analog signal processor 90 or the digital signal processor 94 in certain embodiments. Also, the analog processor 90 and digital processor 94 and their respective output signals 94, 96 form a processor structure 100 that can either be an integrated circuit or chip.

Although the present invention has been shown and described with respect to several preferred embodiments thereof, various changes, omissions and additions to the form and detail thereof, may be made therein, without departing from the spirit and scope of the invention.

What is claimed is:

1. A wearable system for monitoring a plurality of physiological signals associated with a patient, comprising:
   at least one sensor for producing said physiological signals;
   a processor unit for receiving said physiological signals from said at least one sensor, said processor unit analyzing the physiological signals to determine the occurrence of a triggered event and producing at least one output signal identifying the triggered event, the processor unit operable for harvesting RF energy to provide power to the wearable system or only said at least one sensor, said processor unit comprising a plurality of independently programmable channels that generate a plurality of asynchronous spikes when said physiological signals cross a threshold voltage, said at least one output signal is produced after said channels are inputted into a logic array and an output of said array is multiplexed into a single signal; and
   a transmission unit for receiving the at least one output signal and preparing for transmission of the at least one output signal.

2. The wearable system of claim 1, wherein the at least one sensor comprises a plurality of microphones.

3. The wearable system of claim 2, wherein one of the microphones monitors environmental sounds.

4. The wearable system of claim 3, wherein the environmental sounds indicate whether the patient is wearing the wearable system.

5. The wearable system of claim 1, wherein the at least one sensor comprises a plurality of transducers.

6. The wearable system of claim 1, wherein the physiological signals comprise a heartbeat.

7. The wearable system of claim 1, wherein the processor unit comprises an arrangement having a trigger module and digital processor.

8. A method for remotely monitoring a plurality of physiological signals using a wearable system comprising:
   providing at least one sensor producing said physiological signals associated with a patient;
   receiving said physiological signals from said at least one sensor using a processor unit, said processor unit analyzing the physiological signals to determine the occurrence of a triggered event and producing at least one output signal identifying the triggered even, the processor unit harvests RF energy for powering the wearable system or only said at least one sensor, said processor unit comprising a plurality of independently programmable channels that generate a plurality of asynchronous spikes when said physiological signals cross a threshold voltage, said at least one output signal is produced after inputting said channels into a logic array and multiplexing an output of said array into a single signal; and
   sending the at least one output signal to a transmission unit for transmission.

9. The method of claim 8, wherein the at least one sensor comprises a plurality of microphones.

10. The method of claim 9, wherein one of the microphones monitors environmental sounds.

11. The method of claim 10, wherein the environmental sounds indicate whether the patient is wearing the wearable system.

12. The method of claim 8, wherein the at least one sensor comprises a plurality of transducers.

13. The method of claim 8, wherein the physiological signal comprise a heartbeat.

14. The method of claim 8, wherein the processor unit comprises an arrangement having a trigger module and digital processor.

* * * * *